(12) United States Patent
Pellaux et al.

(10) Patent No.: US 8,546,145 B2
(45) Date of Patent: Oct. 1, 2013

(54) FAST SCREENING OF CLONES

(75) Inventors: René Pellaux, Zürich (CH); Marcel Walser, Winterthur (CH); Andreas Jörg Meyer, Frauenfeld (CH); Martin Held, Zürich (CH); Sven Panke, Zürich (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 13/700,269

(22) PCT Filed: May 27, 2011

(86) PCT No.: PCT/EP2011/002619
§ 371 (c)(1),
(2), (4) Date: Jan. 9, 2013

(87) PCT Pub. No.: WO2011/147579
PCT Pub. Date: Dec. 1, 2011

(65) Prior Publication Data
US 2013/0109041 A1 May 2, 2013

(30) Foreign Application Priority Data

May 28, 2010 (EP) .................................... 10005554

(51) Int. Cl.
*G01N 33/48* (2006.01)
(52) U.S. Cl.
USPC ........................................................ 436/63

(58) Field of Classification Search
USPC ........................................................... 436/63
See application file for complete search history.

(56) References Cited

FOREIGN PATENT DOCUMENTS
WO 2006/125458 11/2006

OTHER PUBLICATIONS

International Search Report issued Dec. 6, 2011 in International (PCT) Application No. PCT/EP2011/002619.
Weaver et al., "Microdrop Technology: A General Method for Separating Cells by Function and Composition", Methods: A Companion to Methods in Enzymology, vol. 2, No. 3, Jun. 1991, pp. 234-247.

*Primary Examiner* — Maryam Monshipouri
(74) *Attorney, Agent, or Firm* — Wenderoth, Lind & Ponack, L.L.P.

(57) ABSTRACT

The invention relates to a method of fast identification and isolation of cells featuring a desired phenotype. The phenotype is coupled to the amount of gas-liberating enzymes or increased growth. The cells are encapsulated into microcapsules allowing exchange of solvents through the microcapsule wall, but retaining some or all of the gas formed by gas-liberating enzymes on contact with corresponding substrates. Microcapsules containing increased amounts of gas-liberating enzymes are starting to float and can be separated. The cells are then isolated from the microcapsules according to standard procedures.

17 Claims, 6 Drawing Sheets

FAST SCREENING OF CLONES

This application is a 371 of PCT/EP2011/002619, filed May 27, 2011, which claims foreign priority to European Patent Application No. 10005554.0, filed May 28, 2010.

FIELD OF THE INVENTION

The invention relates to a fast screening of clones using gas-liberating enzymes as markers, whereby the clones are encapsulated and separated based on difference in buoyancy.

BACKGROUND ART

Previously, clone-specific expression of genes coding for gas-liberating enzymes in microbial cells cultivated in microcapsules has been proposed (WO2009/132820) as a method for separation of colonized and non-colonized microcapsules in suspension. In this setting, the genes coding for the gas-forming enzymes are regulated in an identical fashion, i.e. all genes were constitutively expressed. Subsequently, all clones contained similar amounts of gas-liberating enzymes. The method has then been used for the separation of colonized and non-colonized capsules by aid of buoyancy while keeping the microcapsules in suspension.

International patent application WO 2006/125458 describes a method for sequencing of polynucleotides encapsulated in suitable microcapsules.

SUMMARY OF THE INVENTION

The invention relates to a method of fast identification and isolation of cells featuring a particular phenotype, comprising
(a) optionally coupling the expression of the desired particular phenotype to the amount of gas-liberating enzymes in the cells and/or to increased growth of the cells;
(b) encapsulating the cells into microcapsules allowing exchange of solvents through the microcapsule wall but retaining all or a fraction of the gas formed by gas-liberating enzymes;
(c) culturing the microcapsules harbouring the cells under conditions supporting the expression of the particular phenotype and the formation of gas-liberating enzymes;
(d) incubating the microcapsules in a reaction liquor containing a dissolved substrate for the gas-liberating enzymes until gas bubbles are formed in a fraction of the microcapsules;
(e) separating microcapsules floating on the reaction liquor due to the reduction of their specific density caused by gas bubble formation, optionally in a time-dependent manner; and
(f) isolating the cells from the separated microcapsules.

The method of the invention can be applied to natural cells or to recombinant cells wherein expression of a desired particular phenotype is coupled to the expression of dedicated gas-liberating enzymes, for example heterologous carbonate dehydratase or catalase. Alternatively or cumulatively the desired particular phenotype may be coupled to increased growth. In one embodiment, the expression of the desired particular phenotype in one type of cells is coupled to the amount of gas-liberating enzymes in a different type of cells and/or to increased growth of such a different type of cells.

Cells in microcapsules express a catalase gene as a marker for separation of microcapsules harbouring colonies with different cell numbers.

1.1 Microcapsule population after the encapsulation process.
   i: Microcapsule with encapsulated cell(s) from a library.
   ii: Microcapsule carrying no cell.
1.2 Microcapsule population after growth under selective pressure
   ia: Microcapsule with proliferated cells that form a colony
   ib: Microcapsule with cells that did not or only marginally proliferate
   ii: Microcapsule carrying no cells.
1.3 Selection of microcapsules depending on colony size
Left: Microcapsules, as described in 1.2., after growth in aqueous solution.
Right: Added hydrogen peroxide is converted into water and gaseous oxygen by catalase. The formation of an oxygen bubble within the microcapsule is directly dependent on the size of the colony. In the aqueous solution, buoyancy characteristics of microcapsules are directly correlated to the size of the gas bubble which correlates with the colony size.

Figure 1:
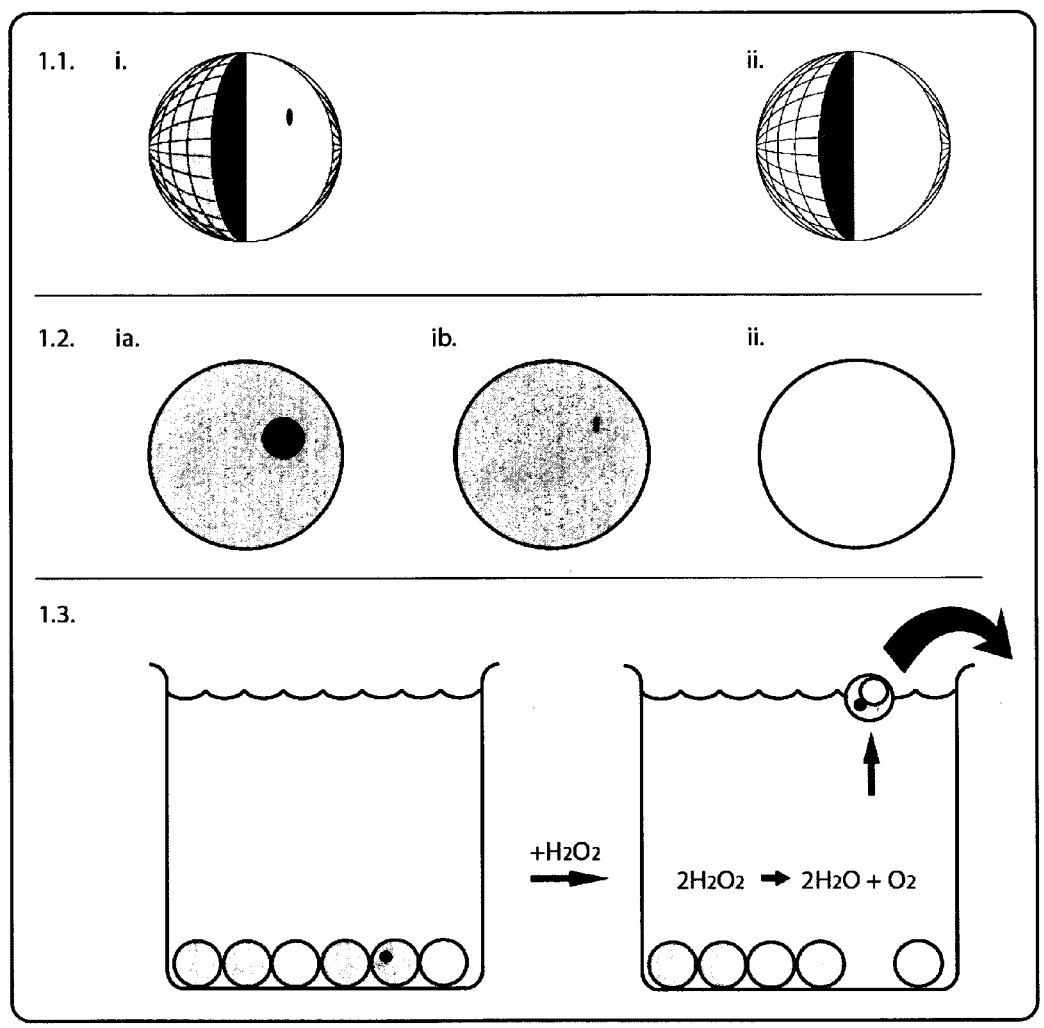
FIG. 1: Separation Based on Growth Under Selective Pressure
Figure 2:
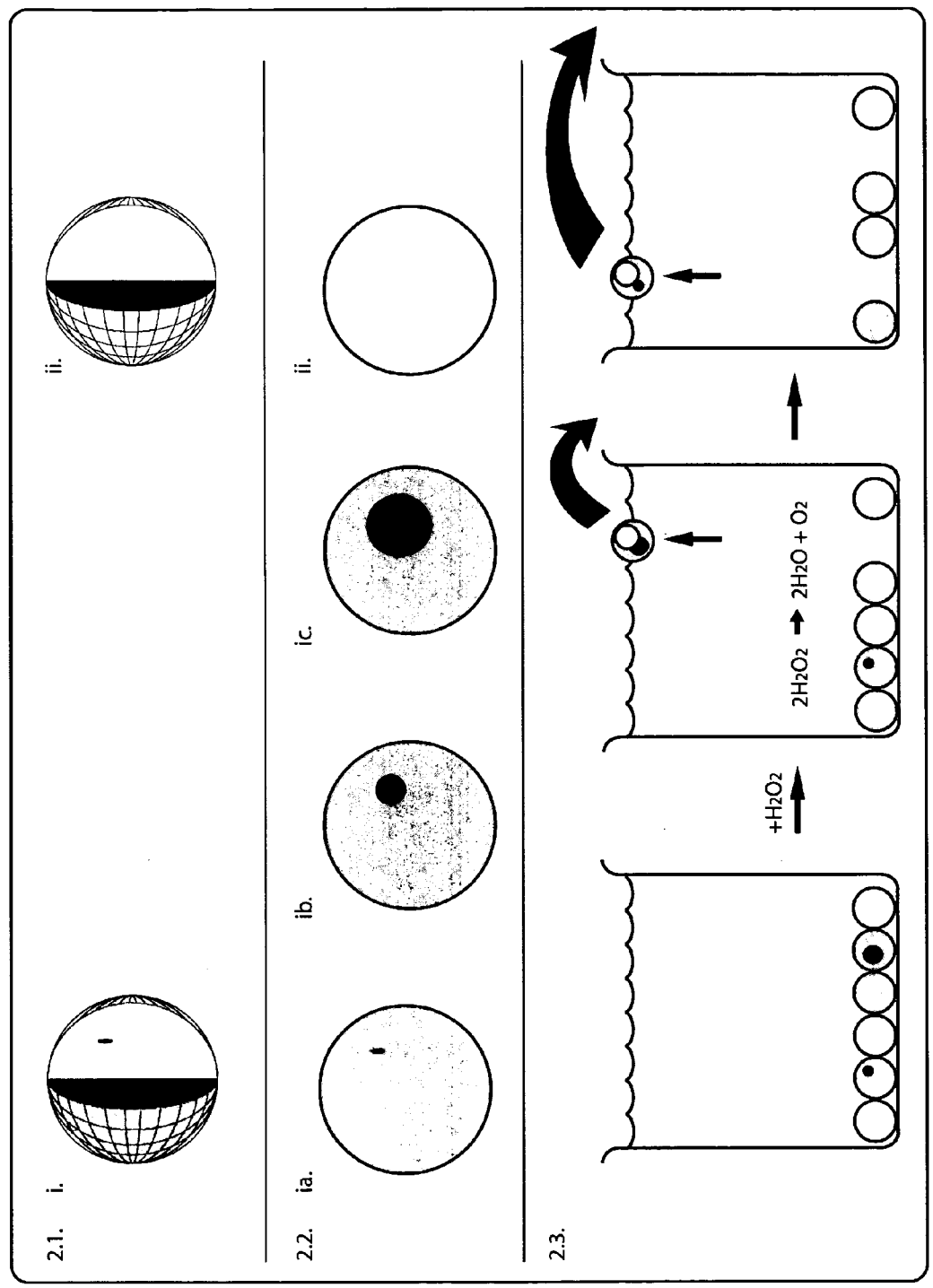

FIG. 2: Fractionation of Clones According to their Colony Size

Figure 3:
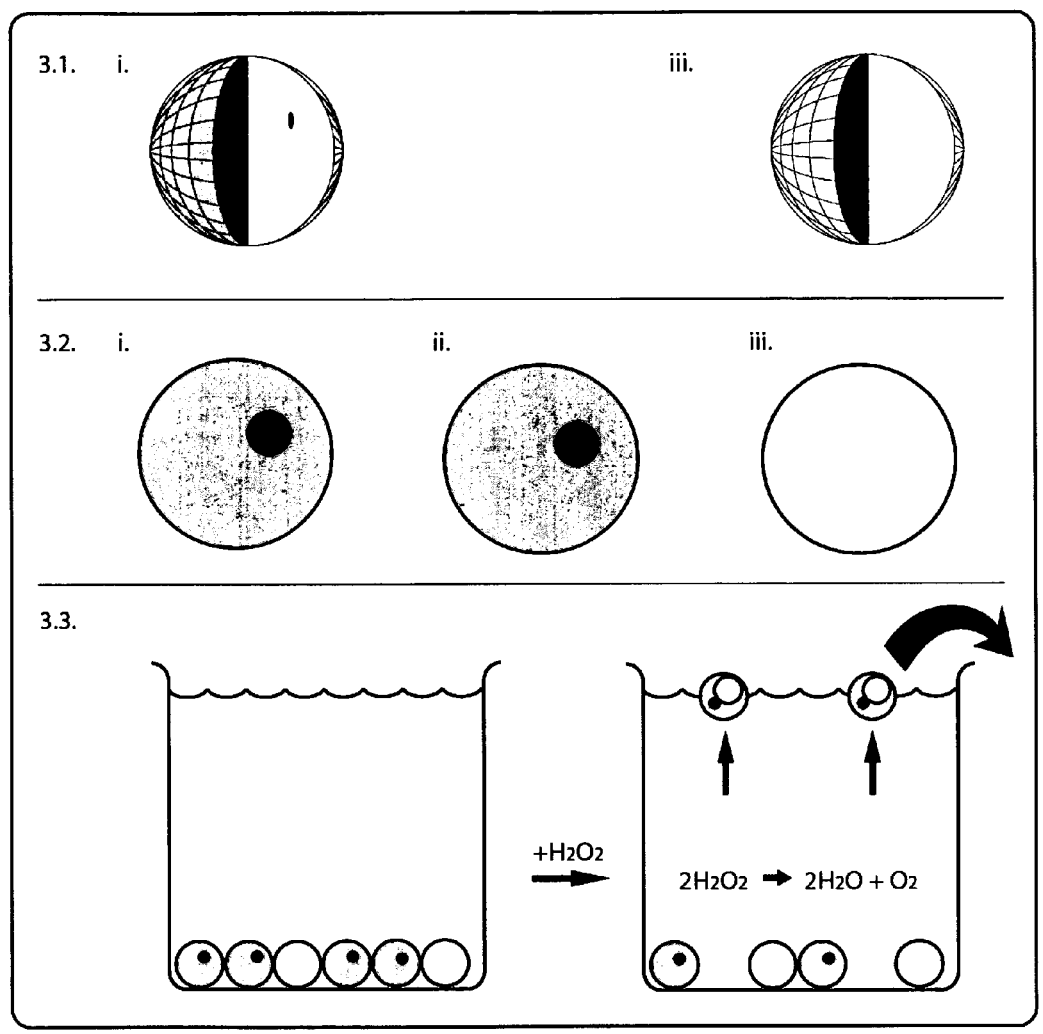

Cells in microcapsules over-express catalase later used as a marker for separation of microcapsules harbouring cellular colonies of various sizes.
2.1 Microcapsule populations after the encapsulation process.
   i: Microcapsule with encapsulated cells.
   ii: Microcapsule carrying no cells.
2.2 Microcapsule populations after growth in a selective medium.
   ia: Cells did not grow in the medium and subsequently did not form a colony.
   ib: Cells grew reasonably well in the medium and formed a small colony.
   ic: Cells grew with high rate in the medium and formed a large colony.
   ii: Empty microcapsules.
2.3 Separation of positive and negative cell clones
Left: Populations of microcapsules harbouring colonies of various sizes after growth (as described in 2.2.) transferred to a beaker.
Middle: The added hydrogen peroxide is converted into water and gaseous oxygen by the colonies. Oxygen bubbles are formed first in those microcapsules that carry a large colony and the respective fraction of microcapsules is recovered from the liquid.
Right: Afterwards microcapsules containing small colonies start to ascend and the respective fraction of microcapsules can be recovered in a separate step.
FIG. 3: Separation by Triggered Gene Expression The controlled expression of a catalase gene is used for selection of positive candidates
3.1 Microcapsule population after encapsulation
   i: Microcapsule with encapsulated cell(s).
   ii: Microcapsule carrying no cell.
3.2 Microcapsule population after growth in the presence of an effector.
   i: Microcapsule with colony with no or minor catalase expression (−).
   ii: Microcapsule with colony with catalase over-expression (+).
   iii: Microcapsule carrying no cell.
3.3 Selection of microcapsules depends on amount of gas-liberating enzymes synthesized by the cells
Left: Microcapsules, as described in 3.2., after growth in an aqueous solution Right: Added hydrogen peroxide is converted into water and gaseous oxygen by catalase. Oxygen bubbles are formed in microcapsules in which the effector triggered the expression of the catalase gene and the microcapsules can be removed from the surface of the solution.

Figure 4:
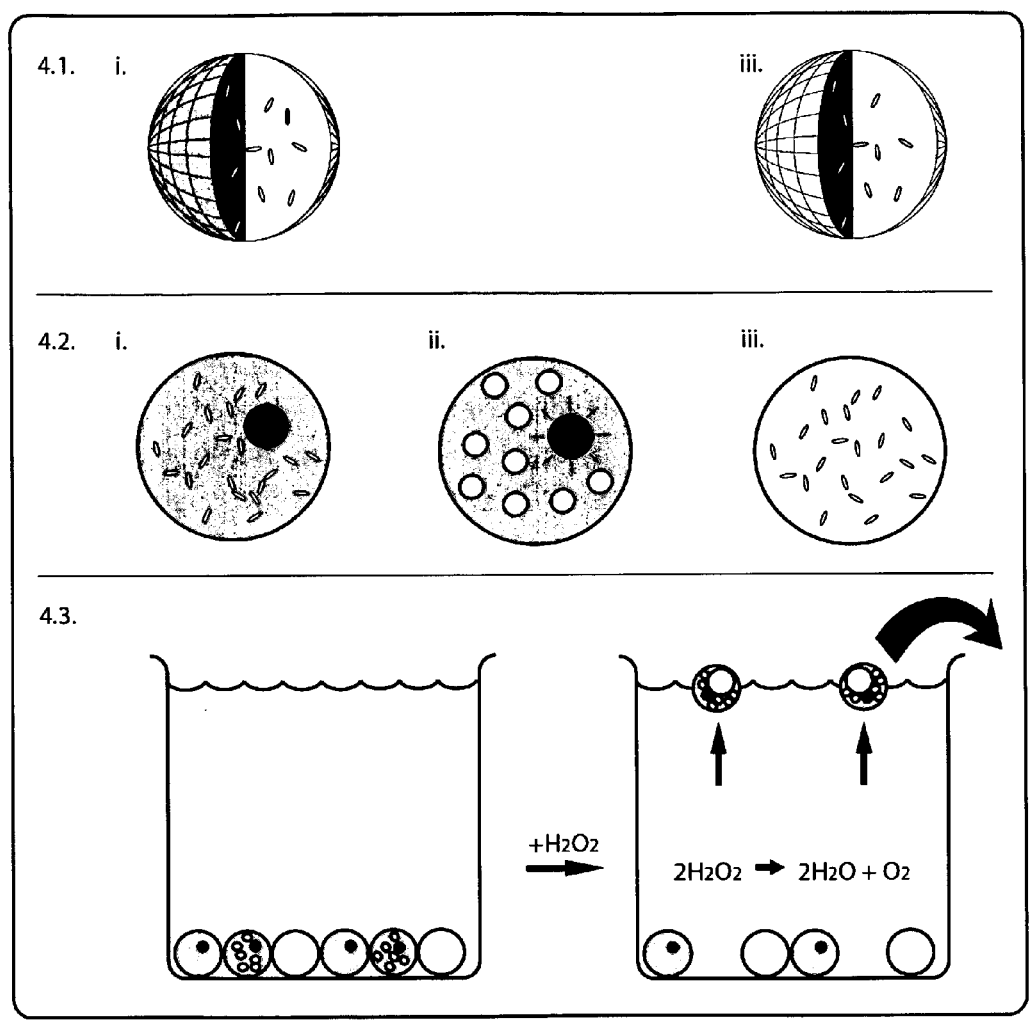

FIG. 4: Separation by Use of a Sensor Strain

Sensor cells expressing a catalase gene are used for the detection of positive candidates.

4.1 Microcapsule population after the encapsulation process.
i: Microcapsule with encapsulated cell(s) and sensor cells. No molecular signal of the cells promotes the proliferation of the sensor cells.
ii: Microcapsule carrying only the sensor cells.

4.2 Microcapsule population after growth phase.
i: Microcapsule with cells (−) that did not promote proliferation of sensor cells.
ii: Microcapsule with cells (+) that promoted proliferation of sensor cells growing colonies.
iii: Microcapsules carrying non-proliferated sensor cells.

4.3 Selection of microcapsules depending on proliferated sensor cells

Left: Microcapsules, as described in 4.2., after growth in an aqueous solution.
Right: Added hydrogen peroxide is converted into water and gaseous oxygen by catalase. Oxygen bubbles are formed in microcapsules harbouring proliferated sensor cells enabling the separation of floating microcapsules. Microcapsules with non-proliferated sensor cells remain at the bottom.

Figure 5:
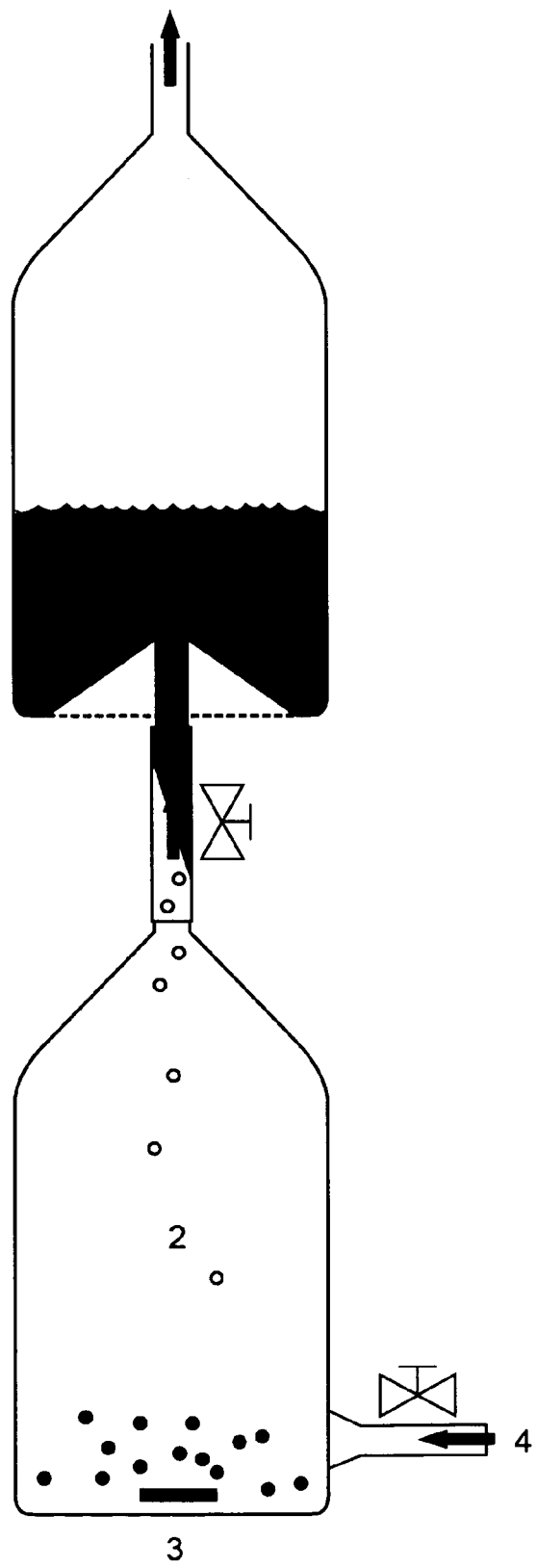

FIG. 5: Device for Selection of Ascending Microcapsules

Device for the isolation and capturing of ascending microcapsules. Hydrogen peroxide is added via the inlet (4) at the bottom of the gently stirred (3) lower chamber (2) filled with an aqueous solute. Ascending microcapsules (carrying oxygen bubbles) pass the narrow funnel between the upper and the lower chamber. After the passage, microcapsules become captured in the upper chamber (1). As the upper chamber contains no or very little hydrogen peroxide at the beginning of the separation process, mean residence times of the ascending microcapsules (containing the positive clones) are kept at a minimum. In this way detrimental effects of $H_2O_2$ on the cells are minimized.

Figure 6:
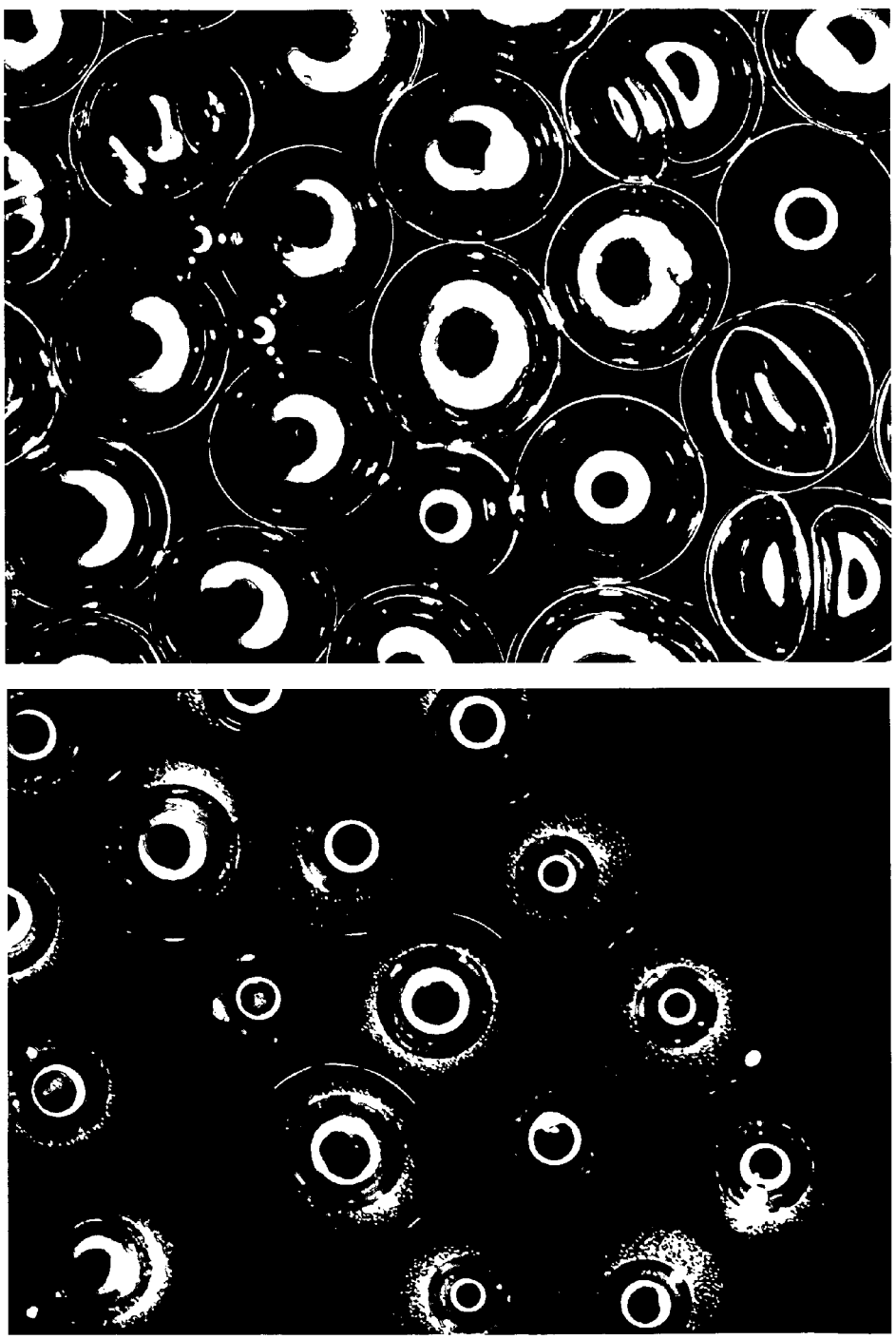

Legend: (1) upper chamber; (2) lower chamber; (3) magnetic stirrer; (4) $H_2O_2$ inlet FIG. 6: Colonized Alginate Microcapsules after Treatment with Hydrogen Peroxide Formation of oxygen bubbles within colonized microcapsules after transformation of $H_2O_2$.
Top: Microscopic picture of oxygen bubbles in microcapsules containing positive cell clones (differential contrast).
Bottom: Fluorescence microscopy of oxygen bubbles in microcapsules containing positive cell clones. The cell clones (small dots under and around the gas bubble) have been stained with SyberGold (excitation: 488 nm; emission: 510 nm).

DETAILED DESCRIPTION OF THE INVENTION

Surprisingly, it was found that the combination of microcapsules and gas-liberating enzymes used as markers can be employed for the identification and isolation of cells featuring a particular phenotype in mixed populations. Even more importantly, the marker can be used for quantitative analyses. Particular features of cells such as up- or down-regulation or de novo establishment of specific pathways, suppression and promotion or certain biochemical reactions, synthesis of enzymes of a desired functionality, or accumulation or synthesis of metabolites or industrial products can be coupled to the expression of gas-liberating enzymes in such a way that a quantitative relationship between the phenotype (and also the desired genotype) and the amounts of gas formed by gas-liberating enzymes is obtained. According to the invention, cells are embedded in microcapsules that have been specifically designed in such a way that larger quantities of gas formed by gas-liberating enzymes are retained. As a result, the specific density of microcapsules containing positive cell clones is decreased. As a consequence, the buoyancy of microcapsules harbouring a positive clone is increased in comparison to the buoyancy of microcapsules that contain negative cell clones. While incubated in a reaction liquor, microcapsules harbouring positive cells start to float whereas microcapsules harbouring only negative cells do not. Positive cells can then readily be separated from the negative cells by one of several techniques well known in the art such as flotation, sieving, decantation and the like.

The invention allows screening of very large numbers of cell clones at unprecedented rates of several billions of analyzed cells per day.

The invention relates to a method of fast identification and isolation of cells featuring a particular phenotype, comprising
(a) optionally coupling the expression of the desired particular phenotype to the amount of gas-liberating enzymes in the cells and/or to increased growth of the cells;
(b) encapsulating the cells into microcapsules allowing exchange of solvents through the microcapsule wall but retaining all or a fraction of the gas formed by gas-liberating enzymes;
(c) culturing the microcapsules harbouring the cells under conditions supporting the expression of the particular phenotype and the formation of gas-liberating enzymes;
(d) incubating the microcapsules in a reaction liquor containing a dissolved substrate for the gas-liberating enzymes until gas bubbles are formed in a fraction of the microcapsules;
(e) separating microcapsules floating on the reaction liquor due to the reduction of their specific density caused by gas bubble formation, optionally in a time-dependent manner; and
(f) isolating the cells from the separated microcapsules.

Unless defined otherwise, technical and scientific terms used herein have the same meaning as commonly understood by one of ordinary skill in the art to which this invention belongs. One skilled in the art will recognize many materials and methods similar or equivalent to those described herein, which could be used in the practice of the present invention. The present invention is in no way limited to the materials and methods described herein. For purposes of the present invention, the following terms are defined below.

The term "cells" refers to prokaryotic, eukaryotic or archaeal cells. Examples for species belonging to the prokaryotic domain of prokaryotic cells comprise *E. coli, B. subtilis, Bacillus cereus, P. putida, R. rhodochrous, S. thyphimurium*, and *C. glutamicum*. Examples for species belonging to the domain of eukaryotic cells and to the regnum fungi are *S. cervisiae, P. pastoris, S. pombe, N. crassa, A. gossypii, A. niger, M. oryzae, M. grisea, Candida albicans* and species belonging to the genera of *Ustilago, Fusarium*, and *Cryptococcus*. Example for cell lines and species belonging to the regnum of animalia derived from higher organisms are CHO cells, hybridoma cells, PerC6 cells, HEK cells, MDCK cells, MDBK cells, COS-7 cells, NS0, Hela cells, and Vero cells. Examples derived from insects are Sf9 cells, Sf21 cells, and High Five cells. Examples for plant cells are BY-2 cells. Cells either proliferate in a regular fashion per se or proliferate since they have been engineered by means of tissue manipulation or other techniques known in the art of biology. Cells according to the invention may be natural cells or cells that do not share the same genotype but have been mutated by one of several methods known in the art of recombinant DNA technology. Examples for methods applied for generation of mutated cells are random mutagenesis (e.g. by UV radiation or chemical mutagenesis), transformation by genetic elements (e.g. by plasmids, vectors, phages, viruses, or artificial chromosomes) obtained for instance from a DNA library, and the like. Upon proliferation, clones of the cells are formed. These clones either grow in the state of single cells or assemble to complex, multicellular structures such as tissue or plant calli.

"Cell clones" as understood herein are the offspring of a cell. Cells of a cell clone belong to the same genotype.

"Positive cell clones" as understood herein are cell clones that do express one or more genes of interest.

A "DNA library" is a collection of DNA fragments that can be stored and propagated in a population of cells by means of molecular cloning. Examples of DNA libraries include cDNA libraries (formed from reverse-transcribed RNA), genomic libraries (formed from genomic DNA), metagenomic libraries (formed from not or poorly defined samples), libraries of gene variants (formed from a pool of modified versions of one or more genes), and expression libraries (formed from a pool of one of more differently regulated genes).

"Genes of interest" as understood herein are genes encoding for proteins that are sought. Examples for such proteins are proteins that transform one or more compounds at a certain rate or that bind one or more compounds with a certain affinity, wherein examples of said compounds to be transformed or bound are primary or secondary metabolites, chemicals, members of chemical libraries, industrial products (e.g. amino acids, vitamins, solvents, acids, antibiotics, pharmaceutically active compounds, building blocks, flavours, and fragrances), polynucleotides, oligonucleotides, polypeptides, cofactors, drugs, drug candidates, and natural products.

"Phenotype", "genotype" and "genes of interest" are interconnected. Presence of a "gene of interest" in a cell or cell clones is equivalent to a desired genotype or phenotype. This genotype will lead to expression of a phenotype characterized by an elevated amount of gas-liberating enzymes.

"Batch" or "batch of microcapsules" refers to microcapsules that are prepared, incubated or subjected to a specific density triggered separation step in a single experiment.

A "microcapsule" as understood herein is a particulate structure, preferably a spherical structure, comprised of a gel-like material. According to the invention, microcapsules fulfil two main functions. First, microcapsules serve as a cultivation compartment for proliferation of cells or cell clones within their interior. Second, microcapsules retain all or fractions of the gas liberated within their interior by the embedded cells or cell clones and thus alter their specific density and therefore their buoyancy characteristics. Microcapsules are produced by one of several techniques known in the art of microcapsule production. All methods employed for microcapsule production rely on techniques for generation of droplets that are then solidified. Examples for methods employed for droplet generation are emulsification methods, e.g. rapid stirring of immiscible solutions of a gel precursor solution in the presence of a carrier solvent or generation of single droplets by a dedicated step (e.g. spraying, flow-focusing, or laminar jet break up induced by vibration or jet cutting). Preferred methods for solidification are cross-linking of polyionic structures by appropriate counter ions, gelling of molten gel precursor solutions by cooling, polymerization of a monomeric or oligomeric gel precursor by formation of covalent chemical bonds, precipitation polymerization, or combinations thereof.

According to the invention, "reaction liquor" is an aqueous solute of a composition that is required in order to allow the gas-liberating enzymes harboured by the microcapsule to transform a non-gaseous substrate to a gaseous compound. In addition to the non-gaseous substrate, said reaction liquor may contain agents required for support and stabilization (e.g. buffers, carbon and energy sources) for the gas formation step or for cell growth or for the separation step of the microcapsules (e.g. tensides, foam forming agents, antifoaming agents, or solid or liquid components that influence the density of the reaction liquor).

"Gas-liberating genes" as understood herein are genes coding for enzymes that liberate a gaseous compound from a substrate.

If to "amount of gas-liberating enzyme" is referred, the total exploited gas-liberation capacity is meant. In most settings, the actual amount of gas-liberating enzymes (e.g. expressed in percent of the total cell protein) corresponds to the total exploited gas-liberation capacity (e.g. expressed in moles of gas formed per unit of time and number of cells). There are however cases wherein the amount of gas-liberating enzyme and the total exploited gas-liberation capacity do not correlate. Examples are cases wherein upon over-expression of genes encoding for gas-liberating enzymes large quantities of miss-folded and therefore inactive protein (e.g. inclusion bodies) are formed. Under these conditions, the amounts of gas-liberating enzymes are high but the total gas-liberation capacities may still be low. Furthermore, cells may synthesize more than one gas-liberating enzyme. Whereas some of these enzymes may have a high specific activity others may have a low activity (e.g. expressed in terms of moles of gas liberated per unit of time and mole of gas-liberating enzyme). An example for an enzyme with a low gas-liberating activity is the cytochrome dependend pyruvate dehydrogenase of *Escherichia coli* (E.C. 1.2.2.2) with a gas-liberation capacity of no more than 200 micromole of carbon dioxide per second and mg of protein. An example for an enzyme featuring a high activity is catalase of *Pisum sativum* (E.G. 1.11.1.6) with a gas-liberation capacity of approximately 1 mole of oxygen per minute and mg of protein. In these cases, cells that have a high amount of a moderately active gas-liberating enzyme and a very low amount of a highly active gas-liberating enzyme will liberate only very little gas even though they do contain a high total amount of gas-liberating enzymes. On the other hand, cells that have a low amount of moderately active gas-liberating enzymes but a slightly elevated amount of highly active gas-liberating enzymes and therefore a rather low total amount of gas-liberating enzymes may feature a high exploitable gas formation capacity. A similar situation can be encountered in cases wherein cells contain a high amount of gas-liberating enzymes which, however, do not liberate any gas due to lack of substrate. Also in these cases, the amount does not reflect the exploitable gas-liberation capacity.

"Dedicated enzymes" or "dedicated gas-liberating enzymes" are enzymes that do not catalyze a reaction required for supply of carbon or energy used for growth. According to the invention, these dedicated enzymes catalyze a reaction that mainly serves the purpose of gas-liberation. Preferably, these enzymes have very high turn-over numbers (in some cases up to a million gas molecules can be generated per molecule of enzyme and second) and subsequently catalyze the gas-liberation reaction in a very fast way exceeding rates of 10 mmol per gram cell dry weight and second. As a result, very large quantities of gas are liberated in a short time. Subsequently, the specific density of microcapsules containing positive cells or cell clones decreases in a very short time. Microcapsules can thus be fractionated in a very short time, typically in the range of seconds or minutes.

"Housekeeping enzymes" or "housekeeping gas-liberating enzymes" are enzymes that are required for supply of carbon or energy for the cell and that liberate gas molecules in the course of their natural function. Gas-liberation rates of these enzymes are typically rather low due to intrinsically low activity. Furthermore, housekeeping enzymes are usually part of larger pathways such as the tricarbonic acid cycle. The rate at which compounds are channelled through these pathways is tightly controlled in most cells, and often the gas-liberating steps are not limiting the flux of compounds through these pathways. As a consequence, gas-liberation rates of housekeeping enzymes in vivo may be much lower than one would assume on the basis of the in vitro enzyme activity data. Gas-liberation rates of housekeeping enzymes and even of the entire plurality of all housekeeping enzymes contained by a cell is thus usually relatively low and hardly exceeds 10 to 20 micromole per gram cell dry weight and second.

"Incubation" as understood herein refers to the process of suspending at least two microcapsules containing at least one cell per microcapsule in an aqueous solute.

"Secondary metabolites" as understood herein refers to organic compounds not directly involved in the normal growth, development or reproduction of organisms. They belong to the chemical classes of polyketides, fatty acids, terpenoids, steroids, phenylpropanoids, alkaloids, glycosylated aglycones, amino acids, peptides, and carbohydrates formed in physiological processes. More specifically they are selected from the group consisting of macrolides, polyacetylenes, prostaglandin hormones, monoterpenoids, essential oils, iridoids, sesquiterpenes, diterpenoides, gibberellin plant growth hormones, triterpenes, steroids, steroide hormones, cortical steroids, vitamins, saponins, ecdysteroids, brassinosteroids, carotenoids, vitamin D metabolites, coumarins, flavonones, anthocyanins, flavones, isoflavanoids, stilbenes, piperidines, pyrrolidine, benzylisoquinoline alkaloids, indole alkaloids, beta-lactam antibiotics, phytoalexins, pheromones, and insect juvenile hormones.

Provided is a method for analysis and isolation of positive cells or cell clones employing buoyancy as a qualitative and quantitative marker for discrimination and isolation of the positive cells of cell clones from negative cells of cells clones. According to the invention, buoyancy differences of positive cells or cell clones and negative ones are employed for identification and separation. The invention is exemplified in detail below.

According to the invention, cell clones are embedded into gel-like microcapsules. The microcapsules are preferably of globular shape and have a preferred diameter of 5 micrometers to 5,000 micrometers, more preferably of 20 to 1,000 micrometers, and even more preferably of 50 to 500 micrometers. Preferred materials for microcapsule synthesis are hydrogels, more preferably hydrogels comprised of alginates, pectinates, carrageenates, agaroses, cellulose derivatives, or acrylic polymers and water. The microcapsule materials are chosen such that the microcapsule walls are readily penetrated by dissolved substrates while a fraction or all of the gases liberated from the embedded positive cell clones is immobilized and forms a gas bubble within the microcapsule.

Some or all cells harboured by the different microcapsules are genetically diverse, i.e. do not share the same genotype. Genetic diversification of the cells can for instance be achieved by means of molecular cloning or mutagenesis. Preferred methods are random mutagenesis, transformation of the cells by plasmids or vectors carrying heterologous or mutated DNA from a DNA library, or introduction of mutations by transposons, by recombination, or by any other method known in the art. Another method of genetic diversification considered is the use of cell clones belonging to different genera. Also considered is the combination of diversification on the species level with genetic diversification achieved by means of molecular cloning or mutagenesis. Furthermore, in one embodiment, microcapsules may harbour diversified cells of one type potentially expressing the desired particular phenotype, and another type of cells liberating gas as a response to the desired particular phenotype of the first type of cells.

The microcapsules preferably contain on average at least 1 cell per 1,000 microcapsules and no more than 1,000 cells per 1 microcapsule, more preferably at least 1 cell per 100 microcapsules and no more than 100 cell clones per 1 microcapsule, and even more preferably at least 10 cell clones per 1 microcapsule and no more than 10 cell clones per 1 microcapsule. In a preferred embodiment microcapsules contain 1,000 to 1 trillion, more preferably 10,000 to 100 billion, and even more preferably 1 million to 10 billion cells per batch of microcapsules.

According to the invention, a key requirement is that the cells carry genes coding for a gas-liberating enzyme. In principle, any gas-liberating enzyme is appropriate as long as the enzyme converts a substrate into a gaseous compound that forms a gas bubble in microcapsules.

In one embodiment, these genes are heterologously expressed genes encoding a dedicated enzyme that liberates gas from a substrate in a single step. Preferred heterologous genes coding for a dedicated gas-liberating enzyme are genes encoding for an enzyme featuring a high catalytic activity as indicated by a turnover number of more than 10,000 moles of gas per mole of enzyme and per second, more preferably of more than 50,000 moles of gas per mole of enzyme and per second, and even more preferably of more than 100,000 moles of gas per mole of enzyme and per second. Preferred classes of dedicated gas-liberating enzymes are carbonate dehydratases (E.C. 4.2.1.1.) and catalases (E.C. 1.11.1.6). Preferred liberated gases are carbon dioxide in case of carbonate dehydratases and oxygen in case of catalase.

According to this embodiment, the method of the invention comprises a further step before the step of encapsulating cells comprising subjecting a cell to recombinant techniques and coupling an individual desired phenotype to increased expression of dedicated gas-liberating enzymes.

In another embodiment, gas-liberating enzymes are derived from the pool of enzymes required for cell growth or cell metabolism, hereinafter referred to as housekeeping enzymes. Examples of housekeeping enzymes are enzymes derived from the pool of enzymes belonging to the central metabolism required for aerobic growth, such as isocitrate dehydrogenase (E.C. 1.1.41), oxoglutarate dehydrogenase (E.C. 1.2.4.1), pyruvate dehydrogenase (1.2.2.2), or pyruvate ferredoxine oxidoreductase (E.C. 1.2.7.1).

Other examples of housekeeping enzymes are enzymes required for anaerobic growth or fermentation (e.g. pyruvate oxidase; E.C. 1.2.3.3.) or enzymes required for metabolization of carbon by specialized organisms (e.g. formate dehydrogenase; E.C. 1.2.2.1, or urease; E.C. 3.5.1.5).

According to this embodiment, the method of the invention may be applied to natural occurring cells or may comprises a further step before the step of encapsulating cells comprising subjecting a cell to recombinant techniques and coupling a desired phenotype to increased growth capacity of the cell.

According to the invention the amount of gas-liberating enzyme per microcapsule varies with the genotype of the embedded cell or cell clones. In a preferred embodiment, microcapsules that contain a positive cell or positive cell clones also contain a higher amount of gas-liberating enzyme than those microcapsules that contain negative cells or clones or no cells at all. As high amounts of gas-liberating enzymes will result in increased amounts of liberated gas, subsequently a gas bubble is rapidly formed and the specific density of the microcapsule therefore decreases. The buoyancy of microcapsules containing positive cells or cell clones therefore increases more rapidly than the buoyancy of the microcapsules containing no cells, or only negative cells or cells clones. Positive cells or cell clones can thus be readily identified and isolated by aid of buoyancy difference of the microcapsules. As apparent, any relative increase of the amount of gas-liberating enzymes is appropriate as long as the amounts of gas liberated by the positive cell clones is sufficient for decreasing the specific density of those microcapsules that harbour a positive cell clone to an extent required for their identification and isolation.

A correlation between the liberated amounts of gas and the phenotype of the cells or cell clones can be obtained in many different ways. Similarly, several techniques can be applied in order to then separate the positive and the negative fractions.

In one embodiment relying on dedicated gas-liberating enzymes, amounts of gas-liberating enzyme per microcapsule are adjusted by controlling the expression of gas-liberating genes by one or more elements of regulatory control. Preferred regulatory elements are riboswitches, regulatory proteins, or transcription factors. Said regulatory elements are used in order to engineer the cells before encapsulating in such a way that specific pathways or proteins are up or down-regulated. The regulation of the said pathways or proteins will then result in an increased amount of gas-liberating enzymes in the positive cells. Provided that the positive as well the negative cells grow at a comparable rate, a higher amount of gas-liberating enzyme accumulates in those capsules that harbour a positive cell clone. As understood by those skilled in the art, any enzyme catalyzing the liberation of a gaseous compound from a substrate can be used, but preferably dedicated enzymes are used. Preferred dedicated enzymes are catalase or carbohydrate dehydratase. In this embodiment, the amount of gas-liberating enzymes per microcapsule in the positive fraction preferably exceeds the amount of gas-liberating enzyme in the negative fraction by a factor of 2 to 10,000, more preferably by a factor of 5 to 1,000 and even more preferably by a factor of 10 to 100. Microcapsules containing positive and negative clones can then be separated in many different ways. In a preferred embodiment, microcapsules containing positive and negative cells are separated in a dedicated step after cell growth. For this dedicated step, cells are preferably incubated in a reaction liquor containing substrates of the said gas-liberating enzymes. The choice of the substrate will depend on the choice of the gas-liberating enzyme and many different combinations are possible, but in a preferred embodiment catalase is used in combination with hydrogen peroxide as a substrate, while carbonate dehydratase is used in combination with carbonic acid or carbonate salts. In these preferred embodiments, incubation times required in order to achieve separation of the positive and the negative fractions are preferably 30 seconds to 5 hours, more preferably 1 minute to 2 hours, and even more preferably 2 to 30 minutes.

In another embodiment making use of housekeeping gas-liberating enzymes, the amount of gas-liberating enzyme per cell is rather constant throughout the entire cell population but the amount of cell clones or cells harboured by each of the individual microcapsules is regulated instead. The cells used in this embodiment have been engineered and designed in such a way that positive cells proliferate at a higher growth rate than negative cells.

Upon incubation of the microcapsules, positive cells thus respond with growth at a high rate while negative cells do not grow at all or grow in an atrophic way. Subsequently, the amount of positive cell clones per microcapsule readily exceeds the amount of negative cell clones. Microcapsules harbouring a positive cell therefore also harbour an elevated amount of cell clones and therefore also an elevated amount of gas-liberating enzyme. In this embodiment, preferably housekeeping enzymes are used as gas-liberating enzymes. During growth, microcapsules containing cells are preferably incubated in reaction liquor supplemented by one or more substrates required for growth or generation of energy. Examples of substrates are sugars, fatty acids, alkanes including methane, acids, alcohols, hydrogen, carbon monoxide, or carbon dioxide. Examples for liberated gases are carbon dioxide, carbon monoxide, methane, and oxygen. In this embodiment, positive cell clones are preferably allowed to grow until colonies of no less than 10 and no more than 5,000,000 cells, more preferably no less than 50 and no more than 1,000,000 cells, and even more preferably no less than 100 and no more than 100,000 cells are formed. Separation of microcapsules harbouring positive clones and empty microcapsules preferably is done concomitant of after incubation and growth. The time required in order to achieve separation due to specific density differences considerably varies within the experimental boundary conditions but preferably does not exceed 1 year and does not fall below 20 minutes. Microcapsules harbouring positive cell clones can then be separated from the top of the solute by one of many techniques routinely applied and apparent to those skilled in the art.

In another embodiment, above mentioned embodiments using dedicated enzymes and using housekeeping enzymes are combined. Normal cells constitutively express dedicated and housekeeping enzymes at a comparable level within each cell. In this particular embodiment the cells have been engineered in such a way that positive cells grow at higher rates then the negative ones. Furthermore the amount of dedicated gas-liberating enzymes per microcapsule is regulated not only via the growth rate, but also by the expression level of the dedicated gas-liberating enzyme. Separation of positive and negative cells is done after incubation and growth of the cells. The growth step and subsequent separation can be performed according to any of embodiments mentioned above.

In yet another embodiment, the expression of the desired particular phenotype in one type of cells is coupled to the amount of gas-liberating enzymes in a different type of cells and/or to increased growth of such a different type of cells. In this embodiment, each microcapsule harbours two type of cells, one potentially expressing the desired phenotype and the other one acting as a sensor cell and liberating gas if the first type of cells indeed expresses the desired phenotype. The response of the sensor cell to expression of the desired phenotype may be increased growth resulting in increased liberation of gas, or up-regulation or synthesis of elevated amounts of gas-liberating enzymes, or both. A particular way of interaction between cells expressing the desired phenotype and sensor cells liberating gas in response may be by certain biomolecules, such as proteins or other metabolites, or chemicals, which are produced and released into the reaction liquor if the desired phenotype is present, and these biomolecules or chemicals then trigger the liberation of gas in the sensor cells. Such interaction between cells is widely known in the art, and applications to cells within microcapsules are described in WO 2009/132820.

A particular aspect of invention is that not only positive and negative cells can be identified, but that also quantitative aspects of cell properties can be determined and fractions of positive clones of different degree can be isolated. Positive cells may for instance grow at different rates while all negative ones do either not grow or grow at considerably lower rates than the slowest growing clone in a positive fraction. Separation of the positive cells can then be done in repetitive cycles and distinct classes of positive cells can be isolated. During separation, first all microcapsules containing a large number of positive cell clones will float. This fraction is recovered first. Afterwards, all microcapsules containing the second largest number of positive cell clones will float and are then recovered. By adjusting the procedure as a function of incubation time, fractions of clones featuring a particular gas-formation capacity and therefore a particular genotype are isolated. As apparent to those skilled in the art, all of the embodiments mentioned above can be adapted such that different classes of positive cells are obtained.

Examples of desired particular phenotypes to be detected and optionally quantified by the method of the invention are formation of enzymes required for cell growth, preferably hydrolases, lipases, epimerases, proteases, esterases and even more preferably cellobiases or phytase, in particular enzymes required for degradation of sugars, polysaccharides, cellulose, methanol, or methane; formation of vitamins, more preferably vitamin $B_1$, vitamin $B_2$, vitamin C, vitamin D, vitamin $B_2$, vitamin E, vitamin $B_{12}$, vitamin K, vitamin $B_5$, vitamin $B_7$, vitamin $B_6$, vitamin $B_3$, and vitamin $B_9$; formation of amino acids, acids, alcohols, or secondary metabolites; synthesis of enzymes required for synthesis of cobalamin, cyanocobalamin, adenosylcobalamin, methylcobalamin, hydroxocobalamin, biotin, pyridoxalphosphate, cholecalciferol, calcidiol, calcitriol, folic acid, pantothenic acid, ascorbic acid, riboflavin, alanine, glutamine, histidine, hydroxyproline, isoleucine, leucine, proline, serine, valine, arginine, trypthophane, aspartic acid, phenylalanine, threonine, glutamic acid, lysine, ethanol, acetic acid, glyoxylic acid, oxalic acid, lactic acid, 3-hydroxypropionic acid, 1,2-propanediol, 1,3-propanediol, propionic acid, acetone, fumaric acid, succinic acid, malic acid, butanoic acid, butanol, 2,3-dihydroxybutane, acetoine, 1,2,4-trihydroxybutane, itaconic acid, citric acid, muconic acid, glycolic acid, or kojic acid; secretion of pharmaceutically active proteins, preferably of insulin, human growth hormone, erythropoietin, granulocyte colony-stimulating factor, follicle stimulating hormone, luteinizing hormone, albumin, alpha-galactosidase A, alpha-L-iduronidase, N-acetylgalactosamine-4-sulfatase, factor VIII, dornase alpha, tissue plasminogen activator, glucocerebroside, interferon, insulin-like growth factor, or recombinant versions thereof; secretion of putatively pharmaceutical active compounds, more preferably of proteins, peptides, antibodies, antibody fragments, saccharides, polyketones, terpenes, or secondary metabolites; or secretion of a substance binding to a g-protein coupled receptor or a receptor tyrosine kinase.

The methods of the invention find use in a large number of applications, e.g. for isolation and identification of cells or clones in the course of screening experiments performed for discovery of novel compounds, traits, drug targets, or biocatalysts. A particular advantage of the selection procedure is that no antibiotic markers are required for selection of the candidate cells, which is of prime importance for many industrial applications due to the large number of concerns that come along with the applications of antibiotic markers for therapeutic applications.

EXAMPLES

Example 1

Screening of DNA Libraries for Cellulase Genes

A novel method for the isolation of cellobiases from metagenomic libraries was developed: A recombinant *E. coli* K-12 expressing the housekeeping cellobiose transporter proteins ChbA, ChbB and ChbC was transformed with a metagenomic DNA library. Furthermore, the cells carried a DNA construct (plasmid vector pCataq containing: ACYC origin of replication, catalase gene of *Listeria seeligeri*, cat gene—chloramphenicol acetyl transferase, Ptac promoter for catalase induction via IPTG, lac 1$^q$ gene for repression of Ptac) expressing a catalase.

The metagenomic library was isolated from cow rumen liquor with standard protocols for DNA extraction and purification. The isolated DNA was then digested by restriction enzymes (BamHI, Bg/II) and ligated into the plasmid vector pUC19 (BamHI digested) for transformation. The transformation efficiency and library diversity scored approx. $10^8$ clones. The transformants were encapsulated into $10^7$ alginate droplets by flow focusing technology (diameter 0.1 mm; hardening in 50 mM $CaCl_2$ for 30 min; RT; 10 clones per capsule on average). The capsules were recovered by sieving, briefly washed (demineralised water), incubated in an LB-based complex medium (Luria Bertani medium diluted 1 to 10 in demineralised water, 10 min, RT), recovered by sieving and incubated in Petri dishes containing a defined minimal medium for selective growth on cellobiose (200 mL, 1 g/L $NH_4Cl$, 1 g/L $Na_2HPO_4$, 0.1 g/L KCl, 1×MT trace elements, 5 mM Tris-HCl pH 7.3, 0.05 g/L tryptone, 0.025 g/L yeast extract, 1 mM $MgSO_4$, 0.1 mM $CaCl_2$, 0.2 mM $SrCl_2$, 4 g/L cellobiose, 30° C.).

A small aliquot of the capsules was regularly sampled and subjected to microscopic analysis. Within the incubation time of 72 hours about one in $10^5$ of the encapsulated *E. coli* recombinants proliferated to a colony (approximately 30 microns in diameter or ~20,000 cells) while the background colonies remained substantially smaller (less than 5 micrometer colony diameter). The entire batch was then recovered by sieving and incubated in a complex medium (4 g/L yeast extract, 1 g/L tryptone, 0.1 mM $BaCl_2$, 10 mM Tris-HCl pH7.0, 37° C., 2 h). This step is necessary in order to boost catalase expression. The microcapsules were then transferred into the lower chamber of a separation device (see FIG. 5) filled with complex medium (4 g/L yeast extract, 1 g/L tryptone, 0.1 mM $BaCl_2$, 10 mM Tris-HCl pH 7.0). Then hydrogen peroxide (1% final concentration) was added to the lower chamber. As a result, oxygen bubbles were formed within those microcapsules that harboured a large colony (i.e. putatively cellobiase positive) while only very small or no oxygen bubbles were formed in those carriers that harboured a cryptically grown colony (putatively not expressing a cellobiase). No bubble formation was observed in non-colonized microcapsules. Due to the subsequent change of the buoyancy characteristics of the microcapsule population, microcapsules containing putatively positive clones started to ascent in the chamber. Due to constructional design aspects of the separation device (see FIG. 5) operating pretty much like a bow net, ascending microcapsules cannot fall-back into the lower chamber once they entered the upper chamber. Furthermore, hydrogen peroxide concentration in the top chamber is lower than in the bottom chamber therefore providing some mode of protection for the cells against the toxic effects of hydrogen peroxide by keeping the residence time of the positive clones in the presence of the high concentrated solution in the bottom chamber low. The upper chamber was removed after 5 minutes (measured from the time of hydrogen addition) and the liquor was poured over a sieve in order to recover those microcapsules that contained putatively cellobiase-positive clones. The microcapsules were excessively washed with $CaCl_2$ (100 mM), suspended in $CaCl_2$ (10 mM; 50 mL), and subjected to particle analysis and sorting (COPAS, Union Biometrica, Holliston Mass.).

The flow cytometer counted and sorted 1051 microcapsules into eleven 96-deep-well plates. M9 minimal medium (1 mL, 0.4% cellobiose, 50 mM ammonium sulfate) was added to the wells and the clones were cultured in the deep-well-plates on a rotary shaker (37° C., 200 rpm, 12 h). After cultivation, the optical density was determined. The results indicated that 957 clones reached an OD600 of at least 2.0. These clones were subjected to a cellobiase assay. For this, an aliquot of 50 µL of the culture was withdrawn, the cells lysed (standard protocols employing lysozyme), transferred to a 96-well plate containing the fluorogenic compound 4-methylumbelliferyl-cellobioside (50 mg per 1 mL of 10 mM phosphate buffer, pH 7), and incubated for 6 hours at RT). The cellobiase activity was then determined in a fluorescence plate-reader (ex: 365 nm, em: 465 nm). The results indicated that in 780 cultures the fluorescence was at least 20 times higher than that of a negative control (*E. coli* without a cellobiase gene). These clones were selected for further characterization by sequencing. For this, the plasmids were isolated (PlasmidPrep Kit by Sigma following supplier's protocol) and sequenced. Afterwards a BLAST search of the obtained sequences was performed. According to the results of the BLAST alignment, 651 clones carried a gene encoding an enzyme with homology greater than 50% to known cellobiases.

Example 2

Screening for a BioB Variant with Improved Activity

Microbial biotin synthesis suffers from notoriously low production rates due to the very low turnover numbers of the last enzyme of the biotin-syntheses pathway. This enzyme, also known as biotin synthase or BioB, catalyzes the formation of the sulfur ring of biotin from the microbial precursor dethiobiotin.

In order to isolate a new BioB variant with improved activity, the bioB gene of an *E. coli* K-12 derivative is isolated and amplified by error-prone PCR at an error frequency of approx. 5 nucleotides per 1000 bp. The resulting PCR products are the ligated into a plasmid vector also containing a catalase gene (E.C. 1.11.1.6). The plasmid library is then transformed by electroporation into an *E. coli* host void of any biotin synthase activity, recovered in LB (1 h; 30° C.), allowed to grow for a limited number of generation in order to eliminate non-transformed cells (2 h on M9 mineral medium with 0.5% glucose, ampicillin, 30° C.) and mixed with 100 mL alginate solution (2% alginate, approx. 50 Mio. cells per liter solution).

Immediately after mixing, the solution is subjected to droplet formation (approx. 200 µm per droplet; laminar jet breakup; droplet formation rate of 1 kHz; synthesis of 5 Mio. beads). The droplets are dripped into an aqueous hardening solution (100 mM $CaCl_2$; RT) and allowed to mature (30 min, RT), briefly washed (0.9% NaCl solution), and then incubated in a mineral medium (100 mM Tris-HCl pH 7; 0.5% glucose, 50 mM ammonia chloride, 5 mM potassium dihydrogen phosphate, 1 mM magnesium sulfate, 1 mM calcium chloride, 1×MT trace element solution, 150 mM sodium chloride, 0.001% thiamine) at 30° C. Upon incubation only those strains that harbour a functional BioB (and subsequently a functioning biotin pathway) grow on the biotin-free medium (10 mL microcapsules per liter of medium) and form a colony comprised of cell clones within the microcapsules. Due to the large error rates of the PCR, only a small fraction of the library strains reassembles a catalytically active BioB mutant enzyme. The microcapsules are recovered from the medium by sieving, briefly washed with water, and suspended in an aqueous solution (100 mL 100 mM tris pH 7, 10 mM $CaCl_2$) in a beaker. Then hydrogen peroxide is added to a final concentration of 1%. Within microcapsules that do harbour a colony, an oxygen bubble is formed within seconds. The buoyancy of these microcapsules increases while those of empty carriers or carriers that contain a cell which did not proliferate do not. To this end, microcapsules that harbour positive clones start to float. The floating microcapsule fraction is then skimmed off the top-phase by hand using a small spoon net.

The catalase reaction is quenched immediately afterwards by washing with water, and the microcapsules are transferred into a lysis buffer (200 mL; 100 mM phosphate; pH 7.2; 0.1% glucose) provided in a beaker. The suspension is then incubated under gentle stirring (magnetic stirring bar, 100 rpm, RT; 2 h) in order to disintegrate the nL-reactors and recover the cells. After the incubation phase, cells are pelleted by centrifugation (5,000×g, 10 min), the top-phase comprised of dissolved alginate and the lysis buffer is discarded and the cell pellet is resuspended in 10 mL of saline (0.9% NaCl in water). The isolated bacteria suspension is plated out on mineral agar plates (2% agar-agar, 0.5% glucose, 50 mM ammonia sulfate, 10 mM phosphate buffer, pH 7). After incubation (48 h; 30° C.) the clones are picked and cultivated in test tubes on mineral medium (M9 with 0.5% glucose; 30° C.; 48 h). The final optical density of all cultures is measured and the biotin content in all cultures that reached an OD600 of 3 is determined. The results are compared to a reference (non-mutated bioB gene in expressed in the same *E. coli* host and grown on the same medium) and the mutated bioB genes in those strains featuring elevated biotin content are sequenced by standard methods.

Example 3

Screening for an *E. coli* Strain with Increased Protein Secretion Capability

For bacterial recombinant protein production, secretion of the product during production is preferred in comparison to intracellular accumulation, due to facilitated product isolation, improved product quality, and elevated yields. Strains with high secretion capacities are thus of great interest for industrial biotechnology. The example illustrates the application of the method of the invention to the isolation of a highly effective protein secreting *E. coli* clone.

The silenced endogeneous type II secretion pathway of *E. coli* MG1655 (gsp locus at 74.5 minutes of the genome) is amplified by PCR methods well known in the art. In order to generate diversity and later select for secretons of an improved activity, the obtained PCR products are subjected to DNA shuffling. The PCR products are digested by DNAse I such that fragments of 50-200 bp are generated. The fragments are purified by a Nucleotide removal Kit (Qiagen) and reassembled in a primerless PCR reaction. After purification the whole reassembled gsp locus is amplified by PCR using Taq DNA polymerase and the resulting DNA is ligated into a BAC (bacterial artificial chromosome) vector. The BAC library is subsequently transformed into an *E. coli* host strain that lacks the gene encoding the nucleoide structuring protein H-NS and that harbours a plasmid encoding for a gene expressing a recombinant insulin containing the transport signal of the endochitinase ChiA.

For the screening of strains with increased secreton activity, the *E. coli* cells harbouring the BAC library are co-encapsulated with *S. cerevisiae* in 500 µm alginate beads according to the protocols described herein. During screening, a *S. cerivisiae* strain fulfills the function of a "sensor strain" and is used for quantification purposes. The strain contains an insulin receptor and up-regulates a catalase gene upon binding of insulin to the receptor. As a result, capsules that contain an *E. coli* strain with increased secretion of ChiA-insulin chimera will also harbour a *S. cerevisiae* colony with an upregulated level of catalase.

The microcapsules are incubated in growth medium (Luria Bertani medium diluted 1 to 10 in water), supplemented with ampicillin, and incubated overnight at 30° C. After inoculation, the microcapsules are isolated by sieving, washed with 10 mM $CaCl_2$/0.9% NaCl and resuspended in a beaker under gentle stirring (magnetic stirrer, 100 mL of LB diluted 1 to 10, RT). A solution of 30% hydrogen peroxide is then added dropwise to the beaker under constant stirring. The alginate beads that float first on the surface of the solution include most oxygen bubbles at the given hydrogen peroxide concentration, and, thus, contain the largest amount of catalase and secreted target protein. The floating beads are subsequently siphoned off and the co-embedded *E. coli* strains are re-isolated. These strains are then thoroughly characterized with respect to the sequence of the gsp operon and their ability to secrete proteins.

The invention claimed is:

1. A method for fast identification and isolation of cells having a particular phenotype, comprising
   (a) encapsulating the cells into microcapsules capable of allowing exchange of solvents through the microcapsule wall but retaining all or a fraction of a gas formed by a gas-liberating enzyme;
   (b) culturing the microcapsules encapsulating the cells under conditions supporting the expression of the particular phenotype and the formation of the gas-liberating enzyme;
   (c) incubating the microcapsules encapsulating the cells in a reaction liquor containing a dissolved substrate for the gas-liberating enzyme until gas bubbles are formed in at least one of the microcapsules encapsulating the cells;
   (d) separating microcapsules encapsulating the cells floating on the surface of the reaction liquor due to a reduction in specific density caused by the gas bubble formation, optionally in a time-dependent manner; and
   (e) isolating the cells from the separated microcapsules encapsulating the cells,
      wherein, optionally, the expression of the particular phenotype is coupled to the amount of the gas-liberating enzyme in the cells and/or to increased growth of the cells.

2. The method of claim 1, wherein the expression of the particular phenotype is coupled to the amount of the gas-liberating enzyme.

3. The method of claim 1, wherein the expression of the particular phenotype is coupled to increased growth of the cells.

4. The method of claim 1, wherein the expression of the particular phenotype is coupled to both the expression of the gas-liberating enzyme and to increased growth of the cells.

5. The method of claim 1, wherein expression of the particular phenotype in the cells is coupled to gas liberation in different cells encapsulated in the same microcapsule.

6. The method of claim 1, wherein in step (d) the microcapsules are separated in a time-dependent manner.

7. The method of claim 1, wherein the gas-liberating enzyme is a carbonate dehydratase or a catalase.

8. The method of claim 1, wherein the gas-liberating enzyme is an enzyme required for cell growth or cell metabolism.

9. The method of claim 8, wherein the gas-liberating enzyme is a central metabolism enzyme required for aerobic growth, anaerobic growth or fermentation, or is an enzyme required for metabolization of carbon.

10. The method of claim 9, wherein the gas-liberating enzyme is selected from the group consisting of isocitrate dehydrogenase (E.C. 1.1.41), oxoglutarate dehydrogenase (E.C. 1.2.4.1), pyruvate dehydrogenase (1.2.2.2), pyruvate ferredoxine oxidoreductase (E.C. 1.2.7.1), pyruvate oxidase (E.C. 1.2.3.3.), formate dehydrogenase (E.C. 1.2.2.1) and urease (E.C. 3.5.1.5).

11. The method of claim 1, wherein the microcapsules comprise water and a member selected from the group consisting of an alginate, a pectinate, a carrageenate, an agarose, a cellulose derivative and an acrylic polymer.

12. The method of claim 1, wherein at least one cell expressing the gas-liberating enzyme proliferates to form a colony upon incubation in the reaction liquor.

13. The method of claim 1, wherein the particular phenotype is
   formation of an enzyme required for cell growth, or
   formation of an enzyme required for degradation of a sugar, a polysaccharide, cellulose, methanol, or methane.

14. The method of claim 1, wherein the particular phenotype is formation of a vitamin, an amino acid, an acid, an alcohol, or a secondary metabolite.

15. The method of claim 1, wherein the particular phenotype is synthesis of an enzyme required for synthesis of cobalamin, cyanocobalamin, adenosylcobalamin, methylcobalamin, hydroxocobalamin, biotin, pyridoxalphosphate, cholecalciferol, calcidiol, calcitriol, folic acid, pantothenic acid, ascorbic acid, riboflavin, alanine, glutamine, histidine, hydroxyproline, isoleucine, leucine, proline, serine, valine, arginine, trypthophane, aspartic acid, phenylalanine, threonine, glutamic acid, lysine, ethanol, acetic acid, glyoxylic acid, oxalic acid, lactic acid, 3-hydroxypropionic acid, 1,2-propanediol, 1,3-propanediol, propionic acid, acetone, fumaric acid, succinic acid, malic acid, butanoic acid, butanol, 2,3-dihydroxybutane, acetoine, 1,2,4-trihydroxybutane, itaconic acid, citric acid, muconic acid, glycolic acid, or kojic acid.

16. The method of claim 1, wherein the particular phenotype is
   secretion of a pharmaceutically active or putatively pharmaceutically active compound, or
   secretion of a protein, a peptide, an antibody, an antibody fragment, a saccharide, a polyketone, a terpene, or a secondary metabolite.

17. The method of claim 1, wherein the particular phenotype is secretion of a substance binding to a g-protein coupled receptor or a receptor tyrosine kinase.

* * * * *